United States Patent [19]

Boussignac et al.

[11] Patent Number: 4,832,024
[45] Date of Patent: May 23, 1989

[54] CARDIO-VASCULAR CATHETER FOR SHOOTING A LASER BEAM

[76] Inventors: Georges Boussignac, 1, allée de Provence; Jean-Claude Labrune, 2, avenue de Guyenne, both of 92160 Antony, France

[21] Appl. No.: 170,105

[22] Filed: Mar. 17, 1988

Related U.S. Application Data

[63] Continuation of Ser. No. 37,541, Apr. 13, 1987, abandoned.

[30] Foreign Application Priority Data

Apr. 29, 1986 [FR] France .................................. 86 06184

[51] Int. Cl.[4] .................................................. A61B 17/36
[52] U.S. Cl. ................................... 128/303.1; 128/395
[58] Field of Search .................................. 128/4–8, 128/303.1, 395–398

[56] References Cited

U.S. PATENT DOCUMENTS

| | | | |
|---|---|---|---|
| 3,437,747 | 4/1969 | Sheldon | 128/6 |
| 3,821,570 | 6/1974 | Marchergan | 128/395 |
| 3,982,541 | 9/1976 | L'Esperance | 128/303.1 |
| 3,991,764 | 11/1976 | Incropera et al. | 128/303.1 |
| 4,176,662 | 12/1979 | Frazer | 128/6 |
| 4,418,688 | 12/1983 | Loeb | 128/6 |
| 4,470,407 | 9/1984 | Hassein | 128/303.1 |
| 4,592,353 | 6/1986 | Daikuzono | 128/303.1 |
| 4,657,014 | 4/1987 | Edelman et al. | 128/303.1 |
| 4,694,828 | 9/1987 | Eichenbaum | 128/303.1 |

FOREIGN PATENT DOCUMENTS 898753 1/1985 Belgium .
85/02101 5/1985 PCT Int'l Appl. .

*Primary Examiner*—Max Hindenburg
*Attorney, Agent, or Firm*—Fisher, Christen & Sabol

[57] ABSTRACT

This invention relates to a catheter for shooting a laser beam, comprising an optical fiber contained in a sheath, as well as an optical system, wherein said optical system obturates the distal end of said sheath, and, between the distal end of said optical fiber and said optical system, there is formed a chamber which is in communication with a supply conduit and with a return conduit for an optically neutral cooling fluid.

16 Claims, 2 Drawing Sheets

CARDIO-VASCULAR CATHETER FOR SHOOTING A LASER BEAM

This application is a continuation of application Ser. No. 037,541, filed Apr. 13, 1987, now abandoned.

The present invention relates to a catheter adapted to be used in particular for the destruction or reduction of obstacles in the circulatory (cardiovascular) system of the human body.

It is known that the eating habits in the Western world have resulted in atherosclerosis becoming a wide-spread disease. It is treated for example by surgical methods, in particular by positioning prostheses of bridges by-passing the obstructed zone, or by the expansion of the atheromatous stenosis by means of balloon probes. However, such operations are only possible in the case of large arteries, A laser is also known to be used for destroying tissues locally, but the practical use of the known apparatus proves to be extremely expensive, as the power required brings about the destruction of the optical fiber conducting the laser beam after a few shots, of which the number depends on the energy brought and the nature and volume of the obstacles.

However, for the small arteries (below the knee), surgery has been ineffective up to the present time. The human cardio-vascular system is in fact a complex system containing vessels of very different diameters, ranging from about 1 millimeter to some centimetres.

It is an object of the present invention to provide an apparatus allowing repeated shots until the atheroma plate has been completely destroyed, even in the case of small vessels.

To that end, according to the invention, the catheter for shooting a laser beam comprising an optical fiber contained in a sheath, as well as an optical system, is noteworthy in that said optical system obturates the distal end of said sheath and in that, between the distal end of said optical fiber and said optical system, there is formed a chamber which is in communication with a supply conduit and with a return conduit for an optically neutral cooling fluid.

Thanks to said cooling fluid, said optical fiber may ensure the transmission of considerable energy for relatively long periods of time. Moreover, due to its simple structure, the catheter according to the invention may be adapted to very small vessels.

It will be noted that Belgian Pat. No. BE-A-898 753 already discloses a catheter of the type comprising an optical fiber contained in a sheath, as well as an optical system. However, in this known catheter, the optical system is arranged at the distal end of said optical fiber and the sheath is open at its distal end with a view to injecting a fluid into the circulatory system. Consequently, the injection of liquid in the sheath for possibly cooling the optical fiber can only be effected accessorily and episodically and only with liquids tolerated by the circulatory system. Such a drawback therefore considerably limits the use of this prior known catheter and the energy that may be transferred without deteriorating said optical fiber.

In accordance with a first embodiment of the catheter according to the invention, the distal end of said sheath is constituted by a tubular head which is obturated by said optical system and into which open out said optical fiber and said supply and return conduits for the cooling fluid.

Said conduits are preferably arranged inside said sheath and connect the proximal and distal ends thereof. At least one of said conduits may be coaxial to said optical fiber.

In a variant embodiment of the catheter according to the invention, the optical system is fast at least with the distal end of an inner sheath element contained in an outer sheath element, said conduits being respectively constituted by the tubular spaces included between said optical fiber and said inner sheath element and between said inner and outer sheath elements, said conduits communicating together thanks to a passage provided in the inner sheath element at the level of said chamber and said conduit between said inner and outer sheath elements being obturated at its distal end.

The invention will be more readily understood on reading the following description with reference to the accompanying drawings, in which.

Figure 1:
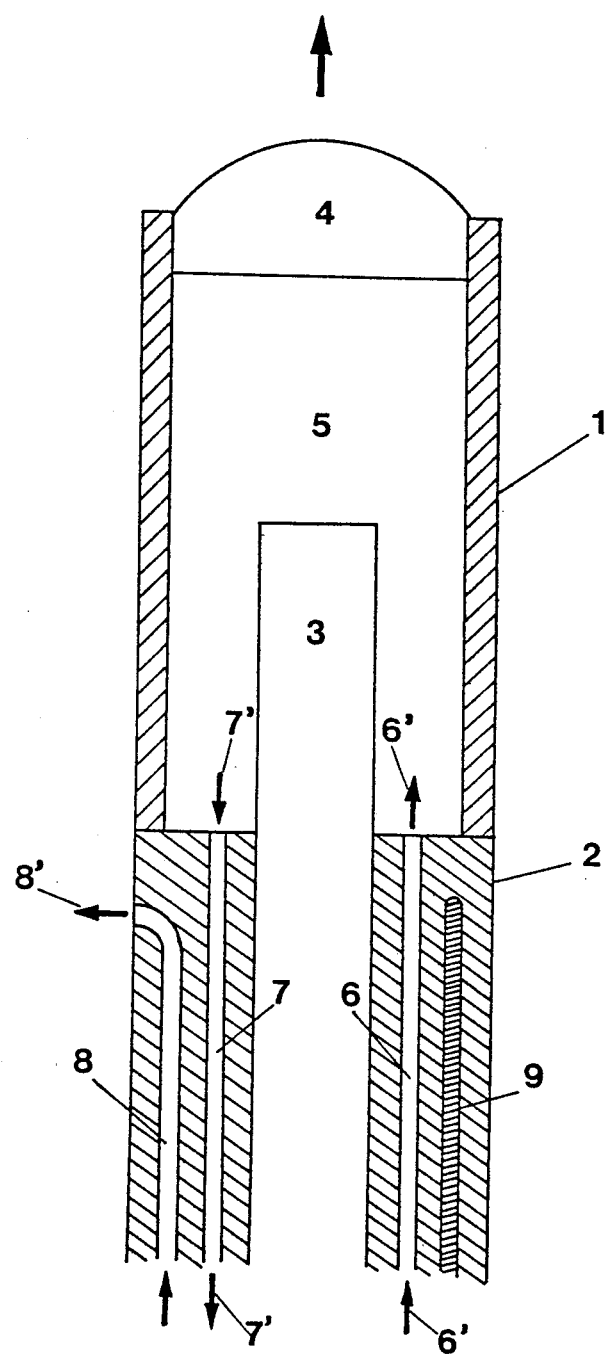
FIG. 1 is an enlarged sectional view of the distal end of a first embodiment of the catheter according to the invention.

Referring now to the drawings, the intermediate parts and the proximal ends of the catheters have not been shown. The same applies to the connections to a laser generator and to a source of cooling fluid, disposed at said proximal ends.

In the embodiment of FIG. 1, the distal end of the catheter is provided with a head 1, fixed or mobile, of generally cylindrical form in continuity with a supple sheath 2.

Into head 1 there opens out an optical fiber 3 of which the proximal end (not shown) may be optically connected to a laser beam, in known manner.

Head 1 is hermetically closed by an optical system 4 intended to protect the optical fiber and to modulate the diameter of the impact of the rays.

Head 1 is intended to perform the role of optical transmission chamber 5 between the fiber 3 and the optical system 4. It is filled with an optically neutral fluid, i.e. one capable of transmitting the energy emitted by the fiber without being modified or decomposed itself.

This same fluid also serves as fluid for cooling the head 1 and the distal end of the fiber 3. It is therefore continuously regenerated, for example by a circulation between the head 1 and a pumping and cooling device (not shown), circulation rendered possible thanks to a supply conduit 6 and a return conduit 7, arranged inside the sheath 2, parallel to fiber 3, and opening out into the head 1. The direction of circulation of the fluid may for example be that illustrated by arrows 6' and 7'.

A fluid having good light- and heat-transmitting properties is for example distilled water or demineralized water.

In any case, it is obvious that the connection between the head 1 and the sheath 2 must prevent the blood from penetrating into the energy transmission chamber 5 due to the risk of self-destruction of the system.

For example, and depending on the materials present, the head 1 may be fast with the sheath 2 by welding, gluing or friction or, if it is provided to be interchangeable, for example by screwing with interposition of a seal, by welding to a possible guide rod 9, or by coupling in situ in the shooting zone.

The matters to be destroyed by light must absorb said light, otherwise destruction is impossible.

In the case of atheromatous plates, virtually white in colour, the incident light is essentially reflected, with the result that the reaction of destruction begins only after a fairly long start-up time, once part of the tissue has changed colour. This is particularly the case with optical fibers of small diameter which can transport only low energy, of the order of 12 to 25 W, for shots of short duration.

In order to accelerate start-up of destruction, it may therefore be desirable to inject a colorant over the zone to be treated. This colorant, coming into contact with the zone to be treated, therefore injected directly into the blood vessel, will for example be haemoglobin more or less diluted with serum. It may be brought onto the zone to be treated for example and preferably via a third conduit 8, likewise incorporated in the sheath 2, opening out in the vicinity (at 8') of the head 1 and supplied upstream by a device such as a pump or a syringe (not shown), disposed on the proximal side of the catheter.

In order to isolate the shooting zone, to centre the optical system and to promote the flow (leaving 8') of the colorant in the direction of the zone to be treated, the catheter may be provided with an inflatable balloon (not shown), of known type, surrounding the sheath 2 upstream of the outlet 8' of the colorant and supplied with swelling fluid by a conduit (not shown) also incorporated in the sheath 2. The technique of inflatable balloon type probes is well known and further explanations are unnecessary for the man skilled in the art.

Said balloon, once inflated, therefore has for a function to force the flow of the colorant in the direction of the zone of impact of the laser ray, but it also serves to block the catheter inside the blood vessel, preventing possible untimely displacements along its axis.

Finally, to overcome the excessive suppleness of the fiber 3 surrounded by its sheath 2, a reinforcing means may also be incorporated in said sheath, such as for example a reinforcement 9 constituted by a material less supple than that of the sheath. It may for example be reinforced by a metal rod or a helically wound metal wire, made of stainless steel, which has the additional advantage of allowing localization of the catheter by radioscopy, when it is in place in a patient's body, and may serve for guiding the probe in certain arteries of the heart.

Although, in FIG. 1, the longitudinal axes of the fiber 3, of the various conduits 6, 7, 8 and of the reinforcement 9, are all shown in the same median plane of the sheath 2, it goes without saying that this representation has been given for reasons of simplification, and that it is preferable to distribute the elements 6, 7, 8 and 9, as well as the supply conduit of a possible balloon (not shown), in relatively regular manner around the central fiber 3, with a view to guaranteeing a better resistance of the whole and to facilitating manufacture thereof.

A further variant consists in shaping one of the conduits 6 or 7 not parallel to and at a distance from the fiber 3, but in giving it ia diameter greater than that of fiber 3 and in rendering it coaxial thereto; in this way, the coolant is in contact with the fiber over virtually the whole of its length.

To ensure a precise position of the distal end of the fiber in the head 1, it is, in that case, expedient to provide, in the vicinity of the zone of connection, in the central conduit, means such as bosses, holding the fiber, but not preventing the passage of the coolant, or to provide the central conduit with a helicoidal groove, in the manner of internal threads in which the fiber 3 is maintained by friction, the coolant following a helicoidal path around and in contact with the fiber.

Figure 2:
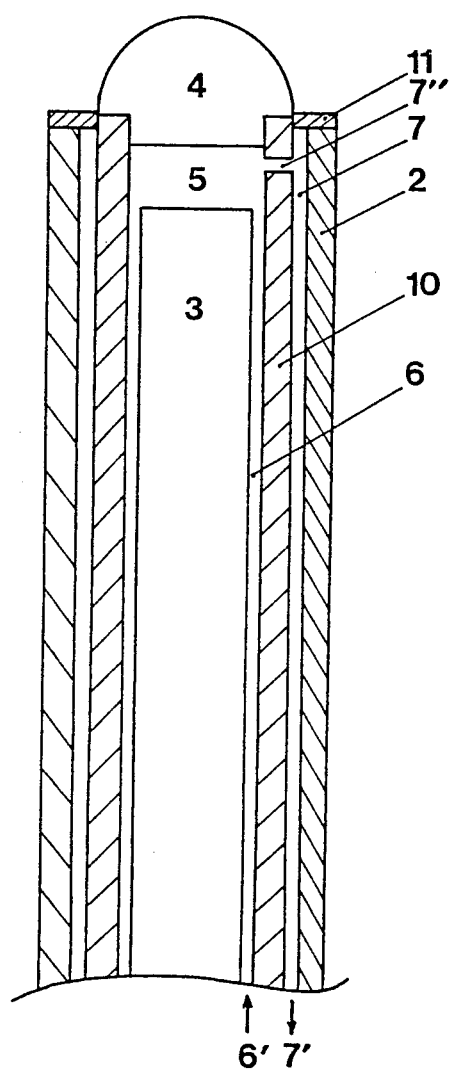
FIG. 2 is an enlarged sectional view of the distal end of a variant embodiment.

A variant embodiment of the catheter of the invention is illustrated in FIG. 2.

In accordance with this variant, the optical system 4 is fast with an inner sheath element 10 containing the optical fiber 3, said inner element 10 being itself contained in an outer sheath element 2. The inner and outer diameters of the inner sheath element 10 are chosen so that the space between the optical fiber 3 and the element 10, on the one hand, and the space between the two elements 10 and 2 on the other hand, constitute coaxial conduits 6 and 7 where the cooling liquid may circulate, said conduits communicating via a passage 7" provided in the sheath 10 at the level of the optical chamber 5. The distal end of the outer element 2 is oburated by the optical system 4. An obturation device 11 ensures seal between the cooling circuit 6, 7 and the outside of the catheter.

The two sheath elements 2 and 10 may possibly be mobile with respect to each other, with the result that, in a first step, only the sheath element 2 can be brought to the site of the lesion to be treated by the conventional technique of vascular catheterism, for example by means of a guide then, in a second step, the inner sheath element 10 bearing the optical system 4 and containing the optical fiber 3 is positioned in the sheath element 2. In this hypothesis, seal being ensured by device 11, the optical chamber should be previously drained by the cooling liquid, in order to drive out any trace of blood pigment before shooting the laser ray.

The materials constituting the various elements of the catheter according to the invention will be easily determined by the man skilled in the art, taking into account the various conditions required: mechanical strength, heat resistance, physiological inertia, optical inertia, etc. . . .

For example, the head 1 may be made of a metal, such as stainless steel, or of ceramic material.

The optical system 4 may for example be made of synthetic sapphire. The outer sheath element 2 may be made of a plastics material such as a polyvinyl chloride, a polytetrafluoroethylene, a polyethylene, etc. . . . It may also be constituted by a steel wire helically coiled with contiguous turns and may be coated externally and internally with polytetrafluoroethylene. The inflatable balloon (not shown) may be made of polyvinyl chloride, silicone rubber or any other appropriate material resisting the required pressure.

The reinforcing and guide rod 9 may be made of stainless steel possibly coated with polytetrafluoroethylene, of tungsten, etc. It may thus be constituted by a wire wound or not around a fine rectilinear blade, possibly mobile, with the result that, by withdrawing said blade, a conduit is formed which may for example be used as return conduit 7.

An additional conduit may possibly be provided for washing the outer surface of the optical system, which conduit may be merged with a conduit intended for containing a guiding device.

For obvious reasons of dimensions of the vessels to be treated, it will in fact be necessary, in certain cases, to reduce the number of conduits and to use, for example, the conduit for the cooling fluid 6 also as conduit for the fluid inflating the balloon.

Finally, it is possible to use the sheath 2 and/or the fiber 3 as a lighting system, in accordance with the well known principle of endoscopes, the optical fiber intended for shooting being able to serve for direct or indirect visualization of the zone to be treated, thanks to an optical device with double opening.

What is claimed is:

1. A cardio-vascular catheter for repeatedly shooting a laser beam in the circulatory system of the human body for a period of time effective to completely destroy localized atheroma plates therein, comprising an optical fiber contained in a sheath, as well as an optical system, wherein said optical system obturates the distal end of said sheath and, between the distal end of said optical fiber and said optical system, there is formed a closed chamber which is in communication with a supply conduit and with a return conduit, which conduits form a closed system for recirculation of an optically neutral cooling fluid.

2. The catheter of claim 1, wherein the distal end of said sheath is constituted by a rigid tubular head obturated by said optical system and into which open out said optical fiber and said fluid supply and return conduits.

3. The catheter of claim 2, wherein it comprises a third conduit opening out in the vicinity of said head and outside the distal end of said sheath, said third conduit serving as a supply conduit for a second fluid.

4. The catheter of claim 1, wherein said cooling fluid supply and return conduits are arranged inside the sheath, parallel to and at a distance from the optical fiber.

5. The catheter of claim 1, wherein at least one of the cooling fluid supply and return conduits is coaxial with the fiber and has a larger diameter than said fiber.

6. The catheter of claim 1, wherein said sheath is reinforced by at least one reinforcement made of a metal material substantially less supple than the material of the sheath and contained within the wall of said sheath.

7. The catheter of claim 6, wherein said reinforcement is a stainless steel rod.

8. The catheter of claim 6, wherein said reinforcement is a helically-wound stainless steel wire encircling said sheath.

9. The catheter of claim 1, wherein the optical system is fast with at least the distal end of an inner sheath element contained in an outer sheath element, said conduits being constituted by the tubular spaces included between the fiber and said inner sheath element, and between said inner and outer sheath elements respectively, said conduits communicating with each other via a passage provided in the inner sheath element at the level of said chamber, and said conduit between said inner and outer sheath elements being obturated at its distal end.

10. The catheter of claim 1 wherein said cooling fluid is distilled water or demineralized water.

11. A cardio-vascular catheter for repeatedly shooting a laser beam in the circulatory system of the human body for a period of time effective to completely destroy localized atheroma plates therein, comprising an optical fiber contained in a sheath, the distal end of said sheath comprising a rigid tubular head obturated by an optical system and forming a closed chamber between the end of said optical system which is in communication with at least one supply conduit and at least one return conduit, which conduits form a closed system for recirculation of an optically neutral cooling fluid for said optical fiber, said conduits being arranged inside said sheath, parallel to and at a distance from said optical fiber, and further comprising a third conduit opening out in the vicinity of said head and outside the distal end of said sheath, said third conduit serving as a supply conduit for a second fluid.

12. A cardio-vascular catheter for repeatedly shooting a laser beam in the circulatory system of the human body for a period of time effective to completely destroy localized atheroma plates therein, comprising an optical fiber contained within a coaxial inner sheath and an outer sheath coaxial thereto and an optical system obturating the distal end of at least said inner sheath, further comprising a closed chamber between the distal end of said optical fiber and said optical system which is in communication with a supply conduit and with a return conduit for an optically neutral cooling fluid for said optical fiber, wherein said conduits are formed by the tubular spaces included between said optical fiber and said coaxial inner sheath and between said coaxial inner and outer sheaths, respectively, said conduits communicating with each other via at least one passage in said inner sheath at the level of said chamber, and said conduit between said inner and outer sheaths being obturated at its distal end.

13. The catheter of claim 12 wherein the inner sheath coaxial to the optical fiber and the outer sheath coaxial with the inner sheath form substantially unobstructed tubular spaces which form said supply conduit and said return conduit.

14. The catheter of claim 12 wherein said inner sheath has at least one helical groove cut or impressed on the inner surface thereof, thereby providing a channel for a helical flow of said cooling fluid over said fiber.

15. the catheter of claim 12 wherein said inner sheath and said outer sheath are movable with respect to each other so that said outer sheath can initially be used for vascular catheterization, and said inner sheath with said optical fiber and said optical system can subsequently be positioned for shooting said laser beam.

16. The catheter of claim 12 wherein at least one of said outer sheath and said optical fiber are used as a lighting system, said optical fiber being adapted for direct or indirect viewing of the treatment zone by means comprising an optical device with a double opening.

* * * * *